(12) United States Patent
Liu et al.

(10) Patent No.: US 10,604,468 B2
(45) Date of Patent: Mar. 31, 2020

(54) APPLICATION OF IONIC LIQUID IN PROPYLENE GLYCOL ETHER SYNTHESIS AND METHOD FOR SYNTHESIZING PROPYLENE GLYCOL ETHER

(71) Applicant: INSTITUTE OF PROCESS ENGINEERING, CHINESE ACADEMY OF SCIENCES, Beijing (CN)

(72) Inventors: Ruixia Liu, Beijing (CN); Suojiang Zhang, Beijing (CN); Ruirui Zhang, Beijing (CN); Junping Zhang, Beijing (CN); Shengxin Chen, Beijing (CN); Fei Dai, Beijing (CN)

(73) Assignee: INSTITUTE OF PROCESS ENGINEERING, CHINESE ACADEMY OF SCIENCES (CN)

( * ) Notice: Subject to any disclaimer, the term of this patent is extended or adjusted under 35 U.S.C. 154(b) by 0 days.

(21) Appl. No.: 15/748,312

(22) PCT Filed: Nov. 14, 2016

(86) PCT No.: PCT/CN2016/105636
§ 371 (c)(1),
(2) Date: Jan. 29, 2018

(87) PCT Pub. No.: WO2017/197857
PCT Pub. Date: Nov. 23, 2017

(65) Prior Publication Data
US 2018/0222833 A1    Aug. 9, 2018

(30) Foreign Application Priority Data

May 20, 2016 (CN) .......................... 2016 1 0341263

(51) Int. Cl.
*C07C 41/03* (2006.01)
*C07C 43/13* (2006.01)
*B01J 31/02* (2006.01)

(52) U.S. Cl.
CPC ........... *C07C 41/03* (2013.01); *B01J 31/0279* (2013.01); *B01J 31/0284* (2013.01);
(Continued)

(58) Field of Classification Search
CPC .... B01J 31/0279; B01J 31/0284; B01J 31/02; B01J 31/0288; C07C 41/03
See application file for complete search history.

(56) References Cited

U.S. PATENT DOCUMENTS

| 8,350,056 B2 | 1/2013 | Du Pont et al. |
| 2015/0027928 A1* | 1/2015 | Likhanova ............. C10G 21/20 208/254 R |

FOREIGN PATENT DOCUMENTS

| CN | 101550069 A  * | 10/2009 | ............. B01J 27/10 |
| CN | 101550069 A | 10/2009 | |

(Continued)

OTHER PUBLICATIONS

Tao et al. ("Synthesis of Tetrabutylphosphonium Carboxylate Ionic Liquids and Its Catalytic Activities for the Alcoholysis Reaction of Propylene Oxide", Industrial & Engineering Chemistry Research, Nov. 2013, vol. 52, Issue 48, pp. 17111-17116).*

(Continued)

*Primary Examiner* — Rosalynd A Keys
(74) *Attorney, Agent, or Firm* — McDonald Hopkins LLC

(57) ABSTRACT

The present invention relates to the technical field of chemical engineering and catalysis. Provided are an application of an ionic liquid in propylene glycol ether synthesis and a method for synthesizing a propylene glycol ether. The ionic liquid is a methyl carbonate ionic liquid, and is used as a (Continued)

catalyst for catalyzing propylene glycol ether synthesis. The method for synthesizing the propylene glycol ether comprises the following steps: placing propylene oxide and an alcohol within a reactor to contact a catalyst, and heating the mixture in an enclosed environment to 50-200° C. to obtain the propylene glycol ether, wherein the catalyst is a methyl carbonate ionic liquid. The method for synthesizing propylene glycol ether provided in the present invention is a green synthesis technique, and does not require special production equipment. The method has simple and easily controllable processes, and can be used in industrial production and applications.

6 Claims, 1 Drawing Sheet

(52) U.S. Cl.
CPC ............ *B01J 31/0288* (2013.01); *B01J 31/02* (2013.01); *B01J 2231/48* (2013.01)

(56) References Cited

FOREIGN PATENT DOCUMENTS

| CN | 102040473 A | 5/2011 | |
|----|----|----|----|
| CN | 105921172 A | 9/2016 | |
| JP | 2014019716 | * 2/2014 | ............ C08B 15/00 |

OTHER PUBLICATIONS

Ravichandran et al. ("Microwave Synthesis—A Potential Tool for Green Chemistry", International Journal of ChemTech Research, Jan.-Mar. 2011, vol. 3, No. 1, pp. 466-470).*

Liang et al. ("The tetramethylguanidine-based ionic liquid-catalyzed synthesis of propylene glycol methyl ether", New Journal of Chemistry, 2010, vol. 34, pp. 2534-2536).*

Holbrey et al. ("Optimised microwave-assisted synthesis of methylcarbonate salts: a convenient methodology to prepare intermediates for ionic liquid libraries", Green Chemistry, 2010, vol. 12, pp. 407-413).*

Zhang et al. (Synthesis of Propylene Glycol Methyl Ether by Grafted Imidazole Basic Ionic Liquids:, Journal of Hebei Normal University/Natural Science Edition, vol. 37, No. 4, Jul. 2013, pp. 382-386).*

International Search Report, dated Feb. 10, 2017; International Patent Application No. PCT/CN2016/105636, filed Nov. 14, 2016; ISA/CN.

* cited by examiner

APPLICATION OF IONIC LIQUID IN PROPYLENE GLYCOL ETHER SYNTHESIS AND METHOD FOR SYNTHESIZING PROPYLENE GLYCOL ETHER

CROSS-REFERENCE TO RELATED APPLICATION

This application is a 35 U.S.C. 371 national stage filing of PCT Application No. PCT/CN2016/105636 filed on Nov. 14, 2016, which claims priority to Chinese Patent Application No. 201610341263.8 filed on May 20, 2016, each of which are incorporated herein in their entirety by reference.

TECHNICAL FIELD

The present disclosure belongs to the field of chemical catalysis, and specifically relates to a use of an ionic liquid in the synthesis of propylene glycol ether and a method for synthesizing propylene glycol ether.

BACKGROUND

Propylene glycol ether is one of the important industrial derivatives of epoxy compounds which mainly produced by the reaction of propylene oxide and an alcohol. Propylene glycol ether has alcohol ether group and hydroxyl group with strong dissolving function, such that it has very strong dissolving property and is known as a universal solvent which is widely used in coating, ink, paint, and printing, etc. Due to steric hindrance effect, the ring-opening position of propylene oxide is different under acidic or alkali condition, so that the addition reaction between the resultant therefrom and an alcohol gives different product, with 1-methoxy-2-propanol being generated under the alkali condition, and 2-methoxy-1-propanol being generated under the acidic condition.

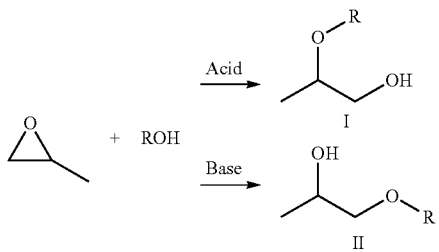

So far, during acidic catalysis, selectivity for resultant is not high, and the ratio of I and II mainly depends on acid strength. Moreover, as the toxicity of product I is higher than that of product II, there has been increasing interest in alkali catalytic synthesis of propylene glycol ether. However, the product of alkali catalysis is predominantly 1-methoxy-2-propanol. According to traditional mechanism, an alkali catalysis reaction is conducted by deprotonation of alcohol under the action of alkali to obtain alkoxy ion, thereafter the alkoxy ion promote the ring-opening of propylene oxide to render an addition reaction. Homogeneous alkali catalyst can be selected from a group consisting of NaOH, NaOR (NaOCH$_3$), NR$_3$ organic amine or NH$_3$, however, all of them have disadvantages such as equipment corrosion and being difficult to recycle.

An ionic liquid generally refers to an organic salt having a melting point below 100° C. It is composed of anion and cation and can have very unique physical and chemical properties by changing the anion and cation, thus it earns more and more attentions. So far, the ionic liquid has been widely used in fields such as electrochemistry, catalysis, and extraction. In the field of catalysis, it is often thought that the ionic liquid as a catalyst can change the reaction pathway. A tetramethylguanidine-based ionic liquid synthesized by Han et al. has higher reactivity and selectivity for the reaction between propylene oxide and an alcohol; however, such kind of ionic liquid is very expensive, limiting its large-scale industrial application.

SUMMARY

The technical problem to be solved by the present disclosure is to overcome the drawbacks in the related technics, and to provide a use of an ionic liquid in the synthesis of propylene glycol ether and a method for synthesizing propylene glycol ether.

The present disclosure provides a use of an ionic liquid in the synthesis of propylene glycol ether, wherein the ionic liquid is methyl carbonate ionic liquid which acts as a catalyst to catalyze the synthesis of propylene glycol ether.

The present disclosure also provides a method for synthesizing propylene glycol ether, which comprises the following steps:

Propylene oxide and an alcohol are fed into a reactor to contact with a catalyst and then heated to 50° C. to 200° C. in a closed environment to obtain propylene glycol ether, wherein the catalyst is methyl carbonate ionic liquid.

The present disclosure provides a use of an ionic liquid in the synthesis of propylene glycol ether, wherein the ionic liquid is methyl carbonate ionic liquid. Methyl carbonate anion-based ionic liquid has been synthesized by Marcin et al. in 2007. Methyl carbonate ionic liquid will react to produce corresponding acid radical under an acidic condition, which avoids the substitution reaction of anion via halogenated ionic liquid as an intermediate to obtain the corresponding anion, thus it is a more environmentally friendly pathway. The mechanism of alkali catalysis of propylene glycol ether is well known in the art, i.e., an addition reaction is occurred subsequent to the ring-opening of propylene oxide. It is often the basic group RO— that causes the ring-opening of propylene oxide, and the basic group is often produced by the dehydrogenation of an alcohol molecule under the action of a catalyst such as KOH and triethylamine. However, for the methyl carbonate ionic liquid provided by the present disclosure, RO— is not resulted from the alcohol molecule, which is different from the traditional mechanism of producing the RO— by the action of a basic group on an alcohol molecule. The ionic liquid itself will self-take off an alkoxy ion under the action of an alcohol molecule. Since the anion of the methyl carbonate ionic liquid is similar to the transition state of transesterification, transesterification will take place between the ionic liquid and an alcohol in the alcoholic solution such that alkoxy group will be taken off from the ionic liquid, then a ring-opening addition reaction will take place on the propylene epoxide via the alkoxy group, as shown in FIG. 1. The present disclosure is based on the pathway by which the RO— is generated from the ionic liquid anion, which catalyzes the reaction between an alcohol and propylene oxide to produce the desired product of propylene glycol ether. The methyl carbonate ionic liquid can catalyze reactions between propylene oxide and various alcohols.

Further, the catalyst is easy to prepare and has low production cost, thus it is suitable for industrial production.

DETAILED DESCRIPTION

The present disclosure will be described in further detail with reference to the accompanying drawings and the embodiments in order to clearly understand the objects, technical solutions and advantages of the present disclosure. It should be understood that the specific embodiments described herein are merely illustrative of the present disclosure and are not intended to limit the present disclosure.

An embodiment of the present disclosure provides a use of an ionic liquid in the synthesis of propylene glycol ether, wherein the ionic liquid is a methyl carbonate ionic liquid which acts as a catalyst to catalyze the synthesis of propylene glycol ether.

Specifically, the alcohol is any one of C1-C8 alcohols, for example an alcohol with an alkyl group having carbon atoms less than or equal to 8 such as methanol, ethanol, propanol, butanol, t-butanol, pentanol, hexanol, heptanol, and octanol. The methyl carbonate ionic liquid is at least one selected from a group consisting of imidazole-based methyl carbonate ionic liquid, quaternary ammonium-based methyl carbonate ionic liquid and quaternary phosphonium-based methyl carbonate ionic liquid. Further, it is preferable that the methyl carbonate ionic liquid is a compound represented by any one of the following structural formulas I-III:

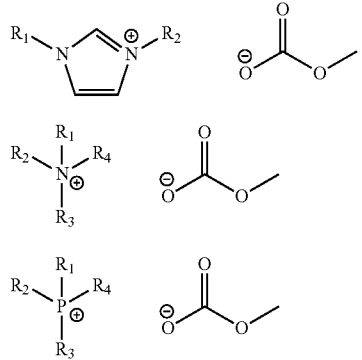

wherein, in the above formulas, $R_1$, $R_2$, $R_3$ and $R_4$ are the same or different $C_1$-$C_{12}$ alkyl.

More preferably, the methyl carbonate ionic liquid is at least one selected from a group consisting of the following ionic liquids: [$N_{2221}$][MC], i.e., $R_1$, $R_2$, $R_3$ and $R_4$ in the structural formula II are $C_2$, $C_2$, $C_2$ and $C_1$ alkyl group, respectively; [$N_{4441}$][MC], i.e., $R_1$, $R_2$, $R_3$ and $R_4$ in the structural formula II are $C_4$, $C_4$, $C_4$ and $C_1$ alkyl group, respectively; [$N_{4444}$][MC], i.e., $R_1$, $R_2$, $R_3$ and $R_4$ in the structural formula II are $C_4$, $C_4$, $C_4$ and $C_4$ alkyl group, respectively; [EMIM][MC], i.e., $R_1$ and $R_2$ in the structural formula I are $C_2$ and $C_1$ alkyl group, respectively; [DMIM][MC], i.e., $R_1$ and $R_2$ in the structural formula I are $C_1$ and $C_1$ alkyl group, respectively; [BMIM][MC], i.e., $R_1$ and $R_2$ in the structural formula I are $C_4$ and $C_1$ alkyl group, respectively. Their structures are as shown below:

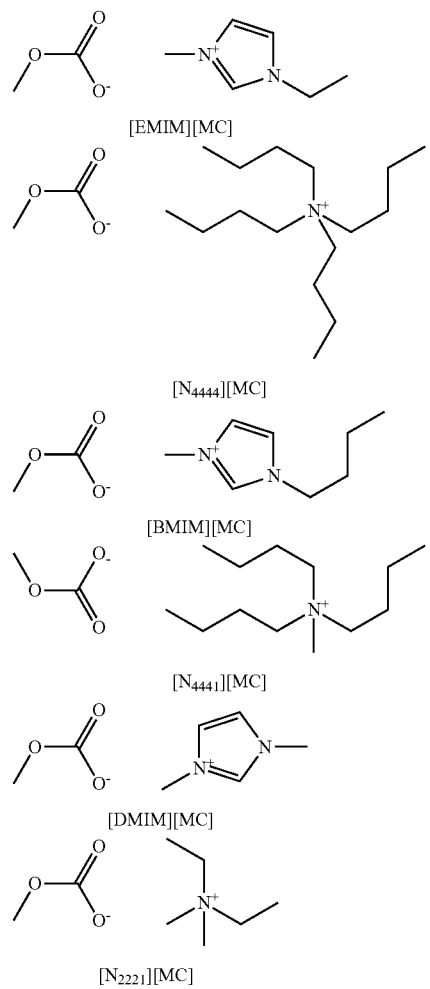

Further, the methyl carbonate ionic liquid is at least one selected from a group consisting of [$N_{2221}$][MC], [$N_{4441}$][MC] and [$N_{4444}$][MC]. In other words, any one or a mixture of two or more of the above ionic liquids can catalyze the synthesis reaction of propylene glycol ether, and have good selectivity and high conversion.

Figure 1:
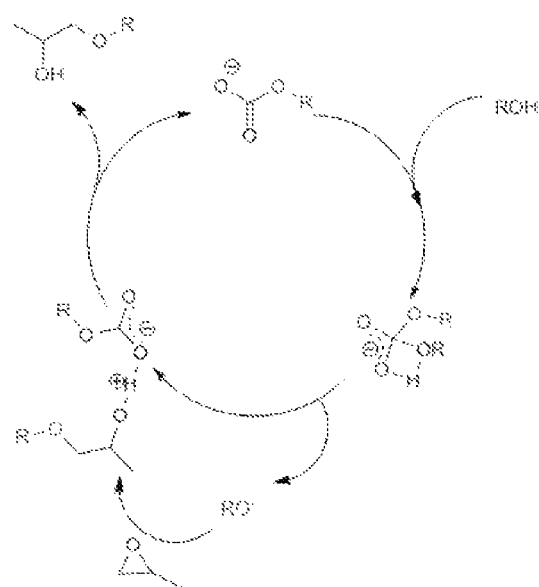
FIG. 1 is a diagram illustrating the mechanism of the reaction between propylene oxide and an alcohol catalyzed by methyl carbonate ionic liquid according to an embodiment of the present disclosure.

After the catalyst [$N_{2221}$][MC] is heated to react in the system of propylene oxide and methanol, it is rotary evaporated and washed with n-hexane solvent for nuclear magnetic characterization. It is shown that the catalyst remains unchanged, i.e. it is still [$N_{2221}$][MC]. The reason for this result is that after the transesterification of methanol with the anion, the exchanged group is still methoxy, so that the anion of the catalyst remains unchanged. It is also shown in the mass spectrum that there is no change in the anion and cation of the ionic liquid. In order to further verify this mechanism, a reaction of ionic liquid [$N_{2221}$][MC] in butanol is carried out under the same condition, wherein the catalyst is treated in the same way after it reacts in the system of propylene oxide and butanol at 80° C. for 4 hours, however, the result is different. It is shown in the nuclear magnetic resonance spectroscopy that the anion of the catalyst has changed and the characteristic peak of the anion has turned into that of butyl carbonate: $^1$H NMR (600 MHZ, DMSO-D6) δ/ppm=0.81 (3H, t, O—CH$_2$CH$_2$CH$_2$CH$_3$), δ/ppm=1.22 (2H, m, O—CH$_2$CH$_2$CH$_2$CH$_3$), δ/ppm=1.31 (2H, m, O—CH$_2$CH$_2$CH$_2$CH$_3$), δ/ppm=3.34 (2H, t, O—CH$_2$CH$_2$CH$_2$CH$_3$). The mass spectrum also shows a peak of butyl carbonate at 117, i.e. ESI-MS: +ve mode: 116.14 ([C$_7$H$_{18}$N]); −ve mode: 117.05 ([C$_5$H$_9$O$_3$]). It is further demonstrated that the methyl carbonate ionic liquid is indeed subjected to transesterification and takes off alkoxy ion in the presence of alcoholic solution. Therefore, the pathway of the reaction has changed. It is no longer the direct ring-opening addition reaction between an alcohol and propylene oxide, but the reaction between the alcohol and an anion under the action of methyl carbonate ionic liquid to release the alkoxy carried by the anion, which then renders a ring-opening addition reaction of propylene oxide, as shown in FIG. 1. This new reaction mechanism strengthens the effect of the catalyst in the reaction, so that both the conversion and the selectivity can be well improved.

Figure 2:
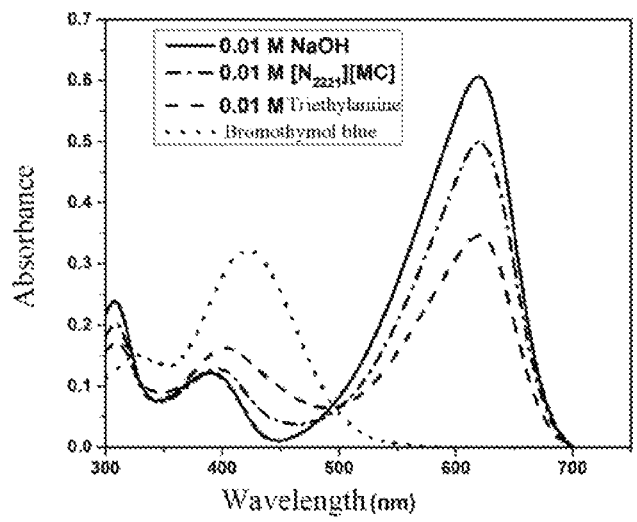
FIG. 2 is a graph showing the UV absorption of bromothymol blue (BTB) and that of BTB after the addition of NaOH, [$N_{2221}$][MC] or triethylamine according to an embodiment of the present disclosure.

The base strength of NaOH, [N$_{2221}$][MC] and triethylamine are measured by using Hammett-UV method with bromothymol blue as an indicator. In the absence of alkali, an absorption peak of hydroxyl group appears at 433 nm, however, after the addition of hydroxy ion, it disappears and a red-shift occurs, resulting in a new absorption peak at 620 nm, as shown in the graph of FIG. 2 showing the UV absorption of bromothymol blue (BTB) and that of BTB after the addition of NaOH, [N$_{2221}$][MC] or triethylamine, wherein the concentration of bromothymol blue is $1.6 \times 10^{-6}$ mol/L. The absorption peak at 620 nm is due to the transfer of hydrogen on the phenolic group of the molecule, its strength increases continuously as the concentration of hydroxy ion increases until a certain extent is reached. A reaction between the bromothymol blue indicator and a large amount of hydroxy ions will cause the leaving of hydrogen at a recognition site, which increases the electron cloud density of the oxygen atom on the phenolic hydroxyl group, further, due to the conjugation of the large it bond on the benzene ring, a charge transfer within the molecule will finally be caused, thereby a new peak at 620 nm is generated and the solution turns into blue. The dissociation constant pK (BTB) of BTB in methanol solution equals to 12.4. For the basic maximum absorption peak at 620 nm, A=0.606, and for the acidic absorption peak, A=0. The Hammett values of NaOH, [N$_{2221}$][MC] and triethylamine in methanol solution calculated by the following formula are as shown in Table 1.

$$H_0 = pK (BTB) + \log([acidic]_s/[basic]_s)$$

Under the same condition, the order of base strength is NaOH>[N$_{2221}$][MC]>triethylamine, which explains the reason why the conversion of methyl carbonate ionic liquid is close to that of a traditional catalyst. Due to different catalytic mechanisms, the [N$_{2221}$][MC] ionic liquid is lower than sodium hydroxide in activity, however its selectivity is greater than sodium hydroxide under the same condition, and 30% higher under certain conditions.

TABLE 1

| | Concentration mol/L | Maximum absorption | Basic (%) | Acidic (%) | Base strength H$_0$ (±0.05) |
| --- | --- | --- | --- | --- | --- |
| NaOH | 0.1 | 0.606 | 100 | 0 | — |
| | 0.01 | 0.605 | 100 | 0 | — |
| | 0.001 | 0.573 | 94.6 | 5.4 | 13.64 |
| [N$_{2221}$][MC] | 0.01 | 0.499 | 82.3 | 17.7 | 13.07 |
| | 0.001 | 0.182 | 30 | 70 | 12.03 |
| Triethylamine | 0.01 | 0.347 | 57.3 | 42.7 | 12.53 |
| | 0.001 | 0.182 | 30 | 70 | 12.03 |

The present disclosure also provides a method for synthesizing propylene glycol ether, which comprises the following steps:

Propylene oxide and an alcohol are fed into a reactor to contact with a catalyst and then heated to 50° C. to 200° C. in a closed environment to obtain the propylene glycol ether, wherein the catalyst is methyl carbonate ionic liquid.

Specifically, the molar ratio of propylene oxide to alcohol is from 1:1 to 1:10, the molar ratio of methyl carbonate ionic liquid to propylene oxide is from 1:1000 to 1:10, and the heating time is from 10 to 300 minutes. The pressure is usually between 0.1 and 1 MPa. Preferably, the molar ratio of propylene oxide to alcohol is from 1:5 to 1:4, and the molar ratio of methyl carbonate ionic liquid to propylene oxide is from 1:50 to 1:200. Further, the heating is preferably microwave heating. The methyl carbonate ionic liquid is at least one selected from a group consisting of an imidazole-based methyl carbonate ionic liquid, a quaternary ammonium-based methyl carbonate ionic liquid and a quaternary phosphonium-based methyl carbonate ionic liquid. Further, it is preferable that the methyl carbonate ionic liquid is at least one selected from a group consisting of [N$_{2221}$][MC], [N$_{4441}$][MC], [N$_{4444}$][MC], [EMIM][MC], [DMIM][MC] and [BMIM][MC]. More preferably, the methyl carbonate ionic liquid is at least one selected from a group consisting of [N$_{2221}$][MC], [N$_{4441}$][MC] and [N$_{4444}$][MC].

The use of an ionic liquid in the synthesis of propylene glycol ether and a method for synthesizing propylene glycol ether will be illustrated by way of the specific examples hereinafter. The ionic liquids in the following examples can be prepared directly according to the existing methods, respectively, and of course, they can also be purchased directly from the market in other examples, and are not limited thereto.

EXAMPLE 1

Synthesis of Ionic Liquid [N$_{2221}$] [MC]:

1.4 g of triethylamine, 3.6 g of dimethyl carbonate (DMC) and 5 mL of methanol were added into a microwave reactor, heated to 120° C., and reacted under magnetic stirring for 6 hours. The reaction products were rotary evaporated to remove a part of the unreacted materials, then washed with n-hexane for three times to remove the unreacted substrates, and after the supernatant liquid was removed, the mixture was placed in a vacuum oven at 50° C. to dry for 24 hours. [N$_{2221}$] [MC] would form a brown yellow crystal at room temperature.

The propylene oxide, methanol and [N$_{2221}$][MC] in a molar ratio of 1:3:0.01 were mixed uniformly, then the mixture was fed into a microwave reaction tube and then heated to 50° C. therein to react for 30 minutes. The obtained mixture was subjected to gas chromatography to determine the composition of the liquid phase mixture, and the conversion of propylene oxide was calculated to be 3.59%, and the selectivity of propylene glycol monomethyl ether was 90.19%.

EXAMPLE 2

The propylene oxide, methanol and [$N_{2221}$][MC] in a molar ratio of 1:3:0.01 were mixed uniformly, then the mixture was fed into a microwave reaction tube and then heated to 70° C. therein to react for 30 minutes. The obtained mixture was subjected to gas chromatography to determine the composition of the liquid phase mixture, and the conversion of propylene oxide was calculated to be 46.62%, and the selectivity of propylene glycol monomethyl ether was 91.78%.

EXAMPLE 3

The propylene oxide, methanol and [$N_{2221}$] [MC] in a molar ratio of 1:3:0.01 were mixed uniformly, then the mixture was fed into a microwave reaction tube and then heated to 80° C. therein to react for 30 minutes. The obtained mixture was subjected to gas chromatography to determine the composition of the liquid phase mixture, and the conversion of propylene oxide was calculated to be 85.64%, and the selectivity of propylene glycol monomethyl ether was 91.09%.

EXAMPLE 4

The propylene oxide, methanol and [$N_{2221}$][MC] in a molar ratio of 1:3:0.01 were mixed uniformly, then the mixture was fed into a microwave reaction tube and then heated to 100° C. therein to react for 30 minutes. The obtained mixture was subjected to gas chromatography to determine the composition of the liquid phase mixture, and the conversion of propylene oxide was calculated to be 99.70%, and the selectivity of propylene glycol monomethyl ether was 87.54%.

EXAMPLE 5

The propylene oxide, methanol and [$N_{2221}$][MC] in a molar ratio of 1:1:0.01 were mixed uniformly, then the mixture was fed into a microwave reaction tube and then heated to 120° C. therein to react for 30 minutes. The obtained mixture was subjected to gas chromatography to determine the composition of the liquid phase mixture, and the conversion of propylene oxide was calculated to be 80.61%, and the selectivity of propylene glycol monomethyl ether was 77.41%.

EXAMPLE 6

The propylene oxide, methanol and [$N_{2221}$] [MC] in a molar ratio of 1:1:0.01 were mixed uniformly, then the mixture was fed into a microwave reaction tube and then heated to 120° C. therein to react for 60 minutes. The obtained mixture was subjected to gas chromatography to determine the composition of the liquid phase mixture, and the conversion of propylene oxide was calculated to be 84.30%, and the selectivity of propylene glycol monomethyl ether was 76.31%.

EXAMPLE 7

The propylene oxide, methanol and [$N_{2221}$] [MC] in a molar ratio of 1:3:0.01 were mixed uniformly, then the mixture was fed into a microwave reaction tube and then heated to 120° C. therein to react for 30 minutes. The obtained mixture was subjected to gas chromatography to determine the composition of the liquid phase mixture, and the conversion of propylene oxide was calculated to be 99.11%, and the selectivity of propylene glycol monomethyl ether was 86.67%.

EXAMPLE 8

The propylene oxide, methanol and [$N_{2221}$][MC] in a molar ratio of 1:3:0.01 were mixed uniformly, then the mixture was fed into a microwave reaction tube and then heated to 120° C. therein to react for 60 minutes. The obtained mixture was subjected to gas chromatography to determine the composition of the liquid phase mixture, and the conversion of propylene oxide was calculated to be 99.56%, and the selectivity of propylene glycol monomethyl ether was 86.67%.

EXAMPLE 9

The propylene oxide, methanol and [$N_{2221}$] [MC] in a molar ratio of 1:3:0.01 were mixed uniformly, then the mixture was fed into a microwave reaction tube and then heated to 120° C. therein to react for 120 minutes. The obtained mixture was subjected to gas chromatography to determine the composition of the liquid phase mixture, and the conversion of propylene oxide was calculated to be 99.78%, and the selectivity of propylene glycol monomethyl ether was 86.54%.

EXAMPLE 10

The propylene oxide, methanol and [$N_{2221}$][MC] in a molar ratio of 1:1:0.01 were mixed uniformly, then the mixture was fed into a microwave reaction tube and then heated to 80° C. therein to react for 60 minutes. The obtained mixture was subjected to gas chromatography to determine the composition of the liquid phase mixture, and the conversion of propylene oxide was calculated to be 88.34%, and the selectivity of propylene glycol monomethyl ether was 74.16%.

EXAMPLE 11

The propylene oxide, methanol and [$N_{2221}$] [MC] in a molar ratio of 1:2:0.01 were mixed uniformly, then the mixture was fed into a microwave reaction tube and then heated to 80° C. therein to react for 60 minutes. The obtained mixture was subjected to gas chromatography to determine the composition of the liquid phase mixture, and the conversion of propylene oxide was calculated to be 94.81%, and the selectivity of propylene glycol monomethyl ether was 84.43%.

EXAMPLE 12

The propylene oxide, methanol and [$N_{2221}$][MC] in a molar ratio of 1:3:0.01 were mixed uniformly, then the mixture was fed into a microwave reaction tube and then heated to 80° C. therein to react for 60 minutes. The obtained mixture was subjected to gas chromatography to determine the composition of the liquid phase mixture, and the conversion of propylene oxide was calculated to be 93.95%, and the selectivity of propylene glycol monomethyl ether was 88.63%.

EXAMPLE 13

The propylene oxide, methanol and [$N_{2221}$] [MC] in a molar ratio of 1:4:0.01 were mixed uniformly, then the mixture was fed into a microwave reaction tube and then heated to 80° C. therein to react for 60 minutes. The obtained mixture was subjected to gas chromatography to determine the composition of the liquid phase mixture, and the conversion of propylene oxide was calculated to be 94.90%, and the selectivity of propylene glycol monomethyl ether was 89.96%.

EXAMPLE 14

The propylene oxide, methanol and $[N_{2221}]$ [MC] in a molar ratio of 1:6:0.01 were mixed uniformly, then the mixture was fed into a microwave reaction tube and then heated to 80° C. therein to react for 60 minutes. The obtained mixture was subjected to gas chromatography to determine the composition of the liquid phase mixture, and the conversion of propylene oxide was calculated to be 91.17%, and the selectivity of propylene glycol monomethyl ether was 91.47%.

EXAMPLE 15

The propylene oxide, methanol and $[N_{2221}][MC]$ in a molar ratio of 1:3:0.01 were mixed uniformly, then the mixture was fed into a microwave reaction tube and then heated to 80° C. therein to react for 120 minutes. The obtained mixture was subjected to gas chromatography to determine the composition of the liquid phase mixture, and the conversion of propylene oxide was calculated to be 99.52%, and the selectivity of propylene glycol monomethyl ether was 91.18%.

EXAMPLE 16

The propylene oxide, methanol and $[N_{2221}]$ [MC] in a molar ratio of 1:3:0.01 were mixed uniformly, then the mixture was fed into a microwave reaction tube and then heated to 80° C. therein to react for 180 minutes. The obtained mixture was subjected to gas chromatography to determine the composition of the liquid phase mixture, and the conversion of propylene oxide was calculated to be 99.92%, and the selectivity of propylene glycol monomethyl ether was 91.53%.

EXAMPLE 17

The propylene oxide, methanol and $[N_{2221}]$ [MC] in a molar ratio of 1:3:0.01 were mixed uniformly, then the mixture was fed into a microwave reaction tube and then heated to 80° C. therein to react for 240 minutes. The obtained mixture was subjected to gas chromatography to determine the composition of the liquid phase mixture, and the conversion of propylene oxide was calculated to be 99.98%, and the selectivity of propylene glycol monomethyl ether was 91.53%.

EXAMPLE 18

The propylene oxide, ethanol and [BMIM][MC] in a molar ratio of 1:1:0.001 were mixed uniformly, then the mixture was fed into a microwave reaction tube and then heated to 50° C. therein to react for 10 minutes. The obtained mixture was subjected to gas chromatography to determine the composition of the liquid phase mixture, and the conversion of propylene oxide was calculated to be 3.12%, and the selectivity of propylene glycol monoethyl ether was 91.31%.

EXAMPLE 19

The propylene oxide, ethanol and [DMIM][MC] in a molar ratio of 1:10:0.1 were mixed uniformly, then the mixture was fed into a microwave reaction tube and then heated to 200° C. therein to react for 300 minutes. The obtained mixture was subjected to gas chromatography to determine the composition of the liquid phase mixture, and the conversion of propylene oxide was calculated to be 99.81%, and the selectivity of propylene glycol monoethyl ether was 90.13%.

EXAMPLE 20

The propylene oxide, butanol and [EMIM][MC] in a molar ratio of 1:1:0.001 were mixed uniformly, then the mixture was fed into a microwave reaction tube and then heated to 50° C. therein to react for 10 minutes. The obtained mixture was subjected to gas chromatography to determine the composition of the liquid phase mixture, and the conversion of propylene oxide was calculated to be 2.31%, and the selectivity of propylene glycol monobutyl ether was 94.54%.

EXAMPLE 21

The propylene oxide, butanol and $[N_{4444}][MC]$ in a molar ratio of 1:1:0.1 were mixed uniformly, then the mixture was fed into a reaction kettle and then heated to 200° C. therein to react for 300 minutes. The obtained mixture was subjected to gas chromatography to determine the composition of the liquid phase mixture, and the conversion of propylene oxide was calculated to be 95.5%, and the selectivity of propylene glycol monobutyl ether was 93.4%.

EXAMPLE 22

The propylene oxide, hexanol and $[N_{4441}][MC]$ in a molar ratio of 1:1:0.001 were mixed uniformly, then the mixture was fed into a microwave reaction tube and then heated to 50° C. therein to react for 10 minutes. The obtained mixture was subjected to gas chromatography to determine the composition of the liquid phase mixture, and the conversion of propylene oxide was calculated to be 2.0%, and the selectivity of propylene glycol monohexyl ether was 95.1%.

EXAMPLE 23

The propylene oxide, hexanol and $[N_{4444}][MC]$ in a molar ratio of 1:1:0.1 were mixed uniformly, then the mixture was fed into a reaction kettle and then heated to 200° C. therein to react for 300 minutes. The obtained mixture was subjected to gas chromatography to determine the composition of the liquid phase mixture, and the conversion of propylene oxide was calculated to be 95.5%, and the selectivity of propylene glycol monohexyl ether was 93.4%.

EXAMPLE 24

The propylene oxide, octanol and [BMIM][MC] in a molar ratio of 1:1:0.001 were mixed uniformly, then the mixture was fed into a reaction kettle and then heated to 80° C. therein to react for 30 minutes. The obtained mixture was subjected to gas chromatography to determine the composition of the liquid phase mixture, and the conversion of propylene oxide was calculated to be 1.5%, and the selectivity of propylene glycol monooctyl ether was 96%.

Example 25

The propylene oxide, octanol and [BMIM][MC] in a molar ratio of 1:1:0.1 were mixed uniformly, then the mixture was fed into a reaction kettle and then heated to 200° C. therein to react for 300 minutes. The obtained mixture was subjected to gas chromatography to determine the composition of the liquid phase mixture, and the conversion of propylene oxide was calculated to be 90.8%, and the selectivity of propylene glycol monooctyl ether was 95.1%.

EXAMPLE 26

The propylene oxide, butanol, [BMIM][MC] and [$N_{22211}$][MC] in a molar ratio of 1:1: 0.05:0.05 were mixed uniformly, then the mixture was fed into a reaction kettle and then heated to 200° C. therein to react for 200 minutes. The obtained mixture was subjected to gas chromatography to determine the composition of the liquid phase mixture, and the conversion of propylene oxide was calculated to be 98.8%, and the selectivity of propylene glycol monobutyl ether was 95.3%.

EXAMPLE 27

The propylene oxide, ethanol, [BMIM][MC] and [$N_{22211}$][MC] in a molar ratio of 1:1: 0.05:0.05 were mixed uniformly, then the mixture was fed into a reaction kettle and then heated to 200° C. therein to react for 200 minutes. The obtained mixture was subjected to gas chromatography to determine the composition of the liquid phase mixture, and the conversion of propylene oxide was calculated to be 99.5%, and the selectivity of propylene glycol monoethyl ether was 93.2%.

EXAMPLE 28

The propylene oxide, butanol, [EMIM][MC], [BMIM][MC] and [$N_{2221}$] [MC] in a molar ratio of 1:1:0.05:0.05: 0.05 were mixed uniformly, then the mixture was fed into a reaction kettle and then heated to 200° C. therein to react for 200 minutes. The obtained mixture was subjected to gas chromatography to determine the composition of the liquid phase mixture, and the conversion of propylene oxide was calculated to be 99.8%, and the selectivity of propylene glycol monobutyl ether was 95.5%.

EXAMPLE 29

The propylene oxide, methanol and [$N_{4444}$][MC] in a molar ratio of 1:7:0.1 were mixed uniformly, then the mixture was fed into a microwave reaction tube and then heated to 80° C. therein to react for 4 hours. The obtained mixture was subjected to gas chromatography to determine the composition of the liquid phase mixture, and the conversion of propylene oxide was calculated to be 98.9%, and the selectivity of propylene glycol monomethyl ether was 92%.

EXAMPLE 30

The propylene oxide, methanol and [BMIM][MC] in a molar ratio of 1:7:0.1 were mixed uniformly, then the mixture was fed into a microwave reaction tube and then heated to 80° C. therein to react for 4 hours. The obtained mixture was subjected to gas chromatography to determine the composition of the liquid phase mixture, and the conversion of propylene oxide was calculated to be 99.3%, and the selectivity of propylene glycol monomethyl ether was 92.1%.

EXAMPLE 31

The propylene oxide, butanol, [EMIM][MC], [BMIM][MC] and [$P_{2221}$][MC] in a molar ratio of 1:1:0.05:0.05:0.05 were mixed uniformly, then the mixture was fed into a reaction kettle and then heated to 200° C. therein to react for 200 minutes. The obtained mixture was subjected to gas chromatography to determine the composition of the liquid phase mixture, and the conversion of propylene oxide was calculated to be 99.6%, and the selectivity of propylene glycol monobutyl ether was 93.5%.

With respect to [$P_{2221}$] [MC] in the present example, $R_1$, $R_2$, $R_3$ and $R_4$ in the structural formula III were $C_2$, $C_2$, $C_2$ and $C_1$ alkyl group, respectively.

EXAMPLE 32

The propylene oxide, butanol, [DMIM][MC], [$N_{8884}$][MC] and [$P_{4444}$] [MC] in a molar ratio of 1:1:0.05:0.05: 0.05 were mixed uniformly, then the mixture was fed into a reaction kettle and then heated to 200° C. therein to react for 200 minutes. The obtained mixture was subjected to gas chromatography to determine the composition of the liquid phase mixture, and the conversion of propylene oxide was calculated to be 94.6%, and the selectivity of propylene glycol monobutyl ether was 91.5%.

With respect to [$N_{8884}$][MC] in the present example, $R_1$, $R_2$, $R_3$ and $R_4$ in the structural formula II were $C_8$, $C_8$, $C_8$ and $C_4$ alkyl group, respectively.

With respect to [$P_{4444}$][MC] in the present example, $R_1$, $R_2$, $R_3$ and $R_4$ in the structural formula III were $C_4$, $C_4$, $C_4$ and $C_4$ alkyl group, respectively.

COMPARATIVE EXAMPLE 1

[$N_{4444}$][Br]: Tributylamine (0.1) and bromo-n-butane (0.2 mol) were added to 100 mL of water, and then the mixture was placed into a high-temperature hydrothermal kettle to react for 12 hours at 90° C. The resulting liquid was rotary evaporated, then washed with diethyl ether for three times and dried in a vacuum oven at 50° C. for 24 hours to obtain the [$N_{4444}$][Br] ionic liquid.

The propylene oxide, methanol and [$N_{4444}$][Br] in a molar ratio of 1:7:0.1 were mixed uniformly, then the mixture was fed into a microwave reaction tube and then heated to 80° C. therein to react for 4 hours. The obtained mixture was subjected to gas chromatography to determine the composition of the liquid phase mixture, and the conversion of propylene oxide was calculated to be 34.4%, and the selectivity of propylene glycol monomethyl ether was 53.8%.

COMPARATIVE EXAMPLE 2

The propylene oxide, methanol and NaOH in a molar ratio of 1:7:0.1 were mixed uniformly, and then the mixture was fed into a microwave reaction tube and then heated to 80° C. therein to react for 4 hours. The obtained mixture was subjected to gas chromatography to determine the composition of the liquid phase mixture, and the conversion of propylene oxide was calculated to be 99.0%, and the selectivity of propylene glycol monomethyl ether was 78.3%.

COMPARATIVE EXAMPLE 3

The propylene oxide, methanol and [BMIM] [Br] in a molar ratio of 1:7:0.1 were mixed uniformly, then the mixture was fed into a microwave reaction tube and then heated to 80° C. therein to react for 4 hours. The obtained mixture was subjected to gas chromatography to determine the composition of the liquid phase mixture, and the conversion of propylene oxide was calculated to be 31.6%, and the selectivity of propylene glycol monomethyl ether was 89.3%.

It can be seen from Example 29 and 30 as well as Comparative Example 1, 2 and 3 that the methyl carbonate anion plays a decisive role in improving the conversion and selectivity, which also indirectly demonstrates that the reaction pathway has changed, and it is no longer the direct ring-opening addition reaction between an alcohol and propylene oxide, but the reaction with the anion under the action of methyl carbonate ionic liquid. The new reaction mechanism strengthens the effect of the catalyst in the reaction, so that both the conversion and the selectivity can be well improved.

The above descriptions are merely the preferred examples of the present disclosure, which are not intended to limit the present disclosure, and any modifications, equivalent substitutions and improvements, etc. made within the spirit and principle of the present disclosure are all encompassed within the protection scope of the present disclosure.

The invention claimed is:

1. A method for synthesizing propylene glycol ether comprising the following steps:
propylene oxide and an alcohol are fed into a reactor to contact with a catalyst and heated to 50° C. to 200° C. in a closed environment to obtain the propylene glycol ether, wherein the catalyst is methyl carbonate ionic liquid, wherein the methyl carbonate ionic liquid is at least one selected from a group consisting of [N$_{2221}$] [MC], [N$_{4441}$][MC], [N$_{4444}$][MC], [EMIM][MC], [DMIM][MC] and [BMIM][MC], and the ionic liquid has the following structural formulas:

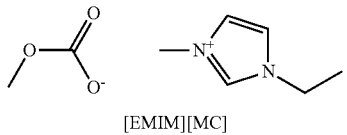

[EMIM][MC]

-continued

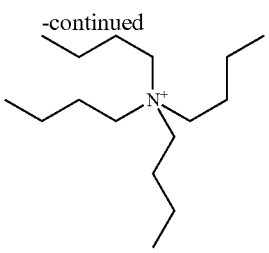

[N$_{4444}$][MC]

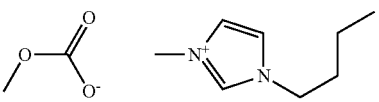

[BMIM][MC]

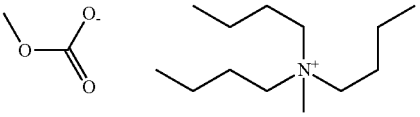

[N$_{4441}$][MC]

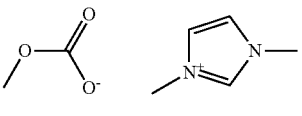

[DMIM][MC]

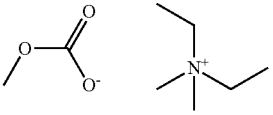

[N$_{2221}$][MC]

wherein the molar ratio of methyl carbonate ionic liquid to propylene oxide is from 1:50 to 1:200.

2. The method for synthesizing propylene glycol ether according to claim 1, wherein the molar ratio of propylene oxide to alcohol is from 1:1 to 1:10.

3. The method for synthesizing propylene glycol ether according to claim 2, wherein the molar ratio of propylene oxide to alcohol is from 1:2 to 1:4.

4. The method for synthesizing propylene glycol ether according to claim 2, wherein the heating time is from 10 to 300 minutes.

5. The method for synthesizing propylene glycol ether according to claim 2, wherein the alcohol is any one of C1-C8 alcohols.

6. The method for synthesizing propylene glycol ether according to claim 2, wherein the heating is microwave heating.

* * * * *